(12) United States Patent
Lindequist

(10) Patent No.: US 6,387,100 B1
(45) Date of Patent: May 14, 2002

(54) METHOD AND ARRANGEMENT FOR POSITION DETERMINING OF BONE STRUCTURE

(75) Inventor: Stig Lindequist, Saltsjöbaden (SE)

(73) Assignee: Medical Robotics i Stockholm AB, Stockholm (SE)

( * ) Notice: Subject to any disclaimer, the term of this patent is extended or adjusted under 35 U.S.C. 154(b) by 0 days.

(21) Appl. No.: 09/647,452

(22) PCT Filed: Mar. 30, 1999

(86) PCT No.: PCT/SE99/00521

§ 371 Date: Nov. 13, 2000

§ 102(e) Date: Nov. 13, 2000

(87) PCT Pub. No.: WO99/49785

PCT Pub. Date: Oct. 7, 1999

(30) Foreign Application Priority Data

Apr. 1, 1998 (SE) ............................................. 9801168
Jun. 10, 1998 (SE) ............................................. 9802052

(51) Int. Cl.[7] ............................................. A61B 17/17
(52) U.S. Cl. ............................. 606/88; 606/86; 606/87; 606/98; 74/490.07
(58) Field of Search ............................. 606/97, 88, 96, 606/86, 87, 89, 90; 74/490.07, 490.03; 248/124.1; 623/16.11

(56) References Cited

U.S. PATENT DOCUMENTS 5,360,446 A * 11/1994 Kennedy ................. 623/16.11
5,569,256 A    10/1996 Vaughn et al.
5,603,243 A *  2/1997 Finley ..................... 74/490.07
5,743,909 A *  4/1998 Collette ........................ 606/88
6,214,013 B1 * 4/2001 Lambrecht et al. ........... 606/96

OTHER PUBLICATIONS

First International Joint Conference Computer Vision, Virtual Reality and Robotics in Medicine and Medical Robotics and Computer–Assisted Surgery Grenoble, France, Mar. 19–22, 1997, TROCCAZ et al: "CVRMed–MRCA'97", pp. 567–569.

* cited by examiner

Primary Examiner—Pedro Philogene
(74) Attorney, Agent, or Firm—Pillsbury Winthrop LLP

(57) ABSTRACT

A positioning determining arrangement used for finding directions for perforations in bone structure surgery is attachable to a machine with a movable arm. The arrangement is provided with a first plate and a second plate, the first and second plates are substantially transparent to X-ray radiation in an orthogonal direction. The first and second plates are mounted in an orthogonal configuration and the first plate is provided with four round elements. The second plate can be mounted to a turnable and tiltable support for attachment t a machine. In this arrangement the X-ray magnification factor relating to two orthogonal X-ray radiographs, comprising the four round elements, taken of a bone structure is determined when two of the four round elements cover each other in both radiographs, the magnification factor being determined by a distance between two uncovered round elements of the four round elements and dependent on movement of the arm.

23 Claims, 9 Drawing Sheets

METHOD AND ARRANGEMENT FOR POSITION DETERMINING OF BONE STRUCTURE

TECHNICAL FIELD

The present invention pertains to a method for aligning an arrangement for marking of directions for perforating together with a position determining arrangement, attached to a machine with a movable arm, in bone structures at surgery, and to said arrangements.

BACKGROUND ART

Present methods regarding, for example, hip fracture surgery involves a great deal of craftsmanship. A patient with an injured leg is placed supine on a fracture table and a reduction maneuver is carried out. The foot of an injured leg is firmly fixed in a specially built shoe. Traction and rotation are applied until the fracture is reduced.

A fixation of an injured leg is normally so firm that no movement will take place unless a substantial force is applied to the leg. A mobile X-ray apparatus, a "C-arm", with two perpendicular radiographs, the anteroposterior (AP) and the lateral (Lat) projections, checks quality of reduction. The result of a reduction can only be judged through said at least two radiographs, and no correction for variations in hip rotation is possible.

Screws are inserted in order to fixate the fractured bone parts. The screws are introduced by a hand-held drill which opens up guide holes for the screws, whereby a surgeon has to judge the position of the drill from said two perpendicular radiographs and manually adjust the position of the drill in three dimensions, which is a very difficult task.

Unfortunately, the insertion of screws very often has to be repeated. Repeated trials of insertion destroy the bone structure in the femoral neck.

To be able to check the quality after a performed hip fracture surgery a method was developed for determining the post surgery position of a fixating means. It was introduced by the inventor of the present invention in his thesis "Internal Fixation of Femoral Neck Fractures", Stockholm 1993, ISBN 91-628-0804-4. Nevertheless, the method has only been used for post-surgery quality checks and scientific statistics, and it has not occurred to or been obvious to any person skilled in the art to modify the method so it can be used in determining how and where to drill in a femoral bone fracture in order to attach fixating means and facilitate healing of said fracture in a best possible way.

Today, orthopedic surgery has promulgated towards sophisticated hi-tech implants being manually inserted through in-precise techniques. To manually insert implants is a task for a highly skilled orthopedic surgeon with, for example, 10 years of training in the present medical field.

For diagnosis groups, where a great number of injuries is accumulated, the result of performed surgery is less satisfactory than it could be. Hip fractures belong to such a group, hereby about 18,000 incidents/year occur in Sweden alone, 9.000 cervical and 9,000 pertrochanteric, to a cost of approximately SEK 1.4 billions.

Despite of the more than 100 different fixating methods developed for this kind of fractures, the result of performed surgery is relatively poor. As much as approximately 35% of all cervical fractures do not heal, and 20% of them have to be re-operated within a time period of 1–2 years. For pertrochanteric fractures the same rates are 10% and 4% respectively. Every re-surgery approximately costs SEK 185.000.

It is agreed with among surgeons and other experts that the main reason for the high percentage of re-surgery is an inadequately positioning of the fixating screws, which hold the fracture together during the following healing process, see "Fixation of femoral neck fractures: comparison of the Uppsala and Von Bahr screws." By Rehnberg & Olerud, Acta Orthop Scand 60, 1989, p. 579–584.

Considering the costs of SEK 185.000 for one re-surgery, a decrease in the rate of such surgery with 50% would gain a save of SEK 160 millions in Sweden a year in surgery costs. A bigger Swedish Hospital would save approximately SEK 8 millions, not to say what is gained in relief for fractured patients.

A known arrangement to support surgery is the so-called ROBODOC™ Surgical Assistant System. The ROBODOC™ robot is able to precisely prepare a femoral channel for placement of a cementless prosthesis.

Due to the manual surgery technique involved in surgery relating to bone fractures and judgements made from said radiographs in real time during surgery/surgical treatment without any tools for performing analysis, the X-ray radiation will be unnecessary high for patients and personnel serving during surgery.

From U.S. Pat. No. 5,603,243 by Finley, an alignment apparatus for aligning X-ray images is known. The apparatus comprises two elongate members in an orthogonal configuration in relation to each other on a supporting framework. Within each member there are four predetermined axes with a plurality of balls mounted on each axis. The balls are preferably of different sizes or are designed to absorb different quantities of X-ray radiation, so that the images of the balls may be recognised individually on an X-ray plate. Since the orientation and spacing of the balls is known, it is possible to determine the precise position and precise orientation of parts of a patient present within an X-ray image through calculation.

The support frame and the elongated members with axes comprising balls provides a fairly complicated apparatus with a lot of calculations for alignment of X-ray images, thus an alignment method or apparatus of simpler construction would be appreciated.

It would be an advantage therefore, to provide a method and arrangements that can aid a surgeon in preparing and supporting orthopedic surgery. Such a method and arrangements are set forth through attached independent claims. Specific embodiments of the invention are introduced through the attached dependent claims. Hence, the method and arrangements of the present invention and details thereof provides such advantages.

SUMMARY OF THE DISCLOSED INVENTION

The present invention aims to solve problems related to determining positions, directions and distances in magnified X-ray images for bone structure surgery.

In order to solve said problems, the present invention sets forth a method for aligning a means for marking of directions for perforating together with position determining means, attached to a machine with a movable arm, in bone structures at surgery, comprising the following steps:

attaching a marking pin to said means for marking, activating said machine and move said means for marking to a defined start position;

assigning said machine a first operation position changing its co-ordinate system so that movement of the marking pin is, approximately, performed within the cross-section of a movable marking pin holder;

aligning said position determining means in relation to said means for marking, said position determining means having at least four round elements;

positioning said position determining means vertical to a reference surface, adjusted so that the marking pin points in a direction, which axis coincides with each round element when the machine moves a specified distance in a square pattern;

placing said position determining means adjacent to the part of the body where the perforation is to be made;

placing an X-ray machine adjusted so that, when radiographs are taken, two of said four round elements cover each other in two orthogonal projection planes;

determining a starting position, whereby said two covered round elements represent the starting position for the machine;

digitizing said radiographs and using the distances between said other non covered round elements in said radiographs, representing the magnification factor, which is calculated and displayed, whereby the magnification factor relates to the movement of the machine arm;

introducing said marking pin through skin and muscles to a position close to the bone structure which is to be perforated;

measuring the distance the marking pin holder has to be moved, thereby giving the machine a second operation position in accordance with the distance the marking pin holder has been moved, whereby the machine arm is able to move around this second position even if the pin and second cylinder is removed, thus all machine movements can take place outside a patients body, but the center of movements will still be close to the bone inside the patients body;

measuring the position of the Marking steel pin, and the lenght to a predetermined marker on said marking pin out off said digitized radiographs, calculating a scale factor for the position of the marker;

marking a desired position for a perforation means in the bone on said digitized radiographs;

comparing a desired position for said perforation means in the bone with the actual position for said marking pin;

making corrections for magnification and scale;

calculating distances and angles that said machine has to move its arm in order to align the marking pin with the perforation position in the bone;

automatic repositioning of the machine in accordance with said calculated distances and angles; and through said machine, performing a perforation of the bone.

In one embodiment the marking pin is changed to a perforator, held by a similar pin holder, said perforator being suitable for drilling, screwing, pinning, milling, grinding or threading.

In another embodiment, a chosen perforator is advanced, by means of said pin holder, so that it enters through the skin and muscles to a position close to the bone.

In a still further embodiment a checking procedure is performed by marking and outlining the direction and position of the perforator and comparing it with the marked perforator position. If the trajectory of the perforator deviates more than a specified distance from the marked desired position, the positioning procedure is redone from the present position, considerably reducing the distances the machine has to move, and therefore reducing positioning errors.

Another embodiment of the present invention comprises that said pin holder is slide-able, and that it is provided in different dimensions with different sizes of a central hole for fitting of marking pins and perforators.

In order to be able to accomplish the aims of the present invention two means are part of the invention.

According to the invention a means for marking of directions and holding of tools for perforation in bone structure surgery, for attachment to a machine with a movable arm is set forth It comprises an outer casing with an aperture for holding an inner casing, one of said casings being slide-able in relation to said movable arm, said inner casing having an attachment for holding perforation means. It is attached to a turnable support or a turnable and tiltable support on said machine.

In one embodiment the slidable casing is electrically actuated to move back and forth.

Another embodiment comprises that one of said casings is revolving for drilling, grinding, milling or other movement used during perforation.

A still further embodiment encompasses that the attachment is able to fit a machine for drilling, grinding, milling or other movement used during perforation.

According to the invention a position determining means used for finding directions for perforation in bone structure surgery, attached to a machine with a movable arm is set forth. It is provided with a first plate and a second plate, both plates being substantially transparent to X-ray radiation in an orthogonal direction, and mounted in an orthogonal configuration, said first plate being provided with four round elements, said second plate being mounted on a turnable and tiltable support for attachment to said machine or initially attached, whereby an X-ray magnification factor relating to two orthogonal X-ray radiographs, comprising the round elements, taken of the bone structure is determined when two of said round elements cover each other in both radiographs, said magnification factor being determined by the distance between said two uncovered round elements and dependent on the movement of said machine arm.

In one embodiment of the position determining means according to the present invention a turn-able support is mounted on a movable frame of said machine, whereby it can be placed in front of means for marking of directions and holding of tools for perforation on said machine.

In another embodiment of the invention the round elements are opaque to X-ray radiation. The round elements are made out of materials opaque to X-ray radiation such as tantalum, lead, steel etc alloys of said materials.

In a preferred embodiment of the invention said round elements are placed in a square configuration on said first plate.

BRIEF DESCRIPTION OF THE DRAWINGS

For a more complete understanding of the present invention and for further objectives and advantages thereof, reference may now be had to the following description in conjunction with the accompanying drawings, in which.

DETAILED DESCRIPTION OF PREFERRED EMBODIMENTS

Figure 1:
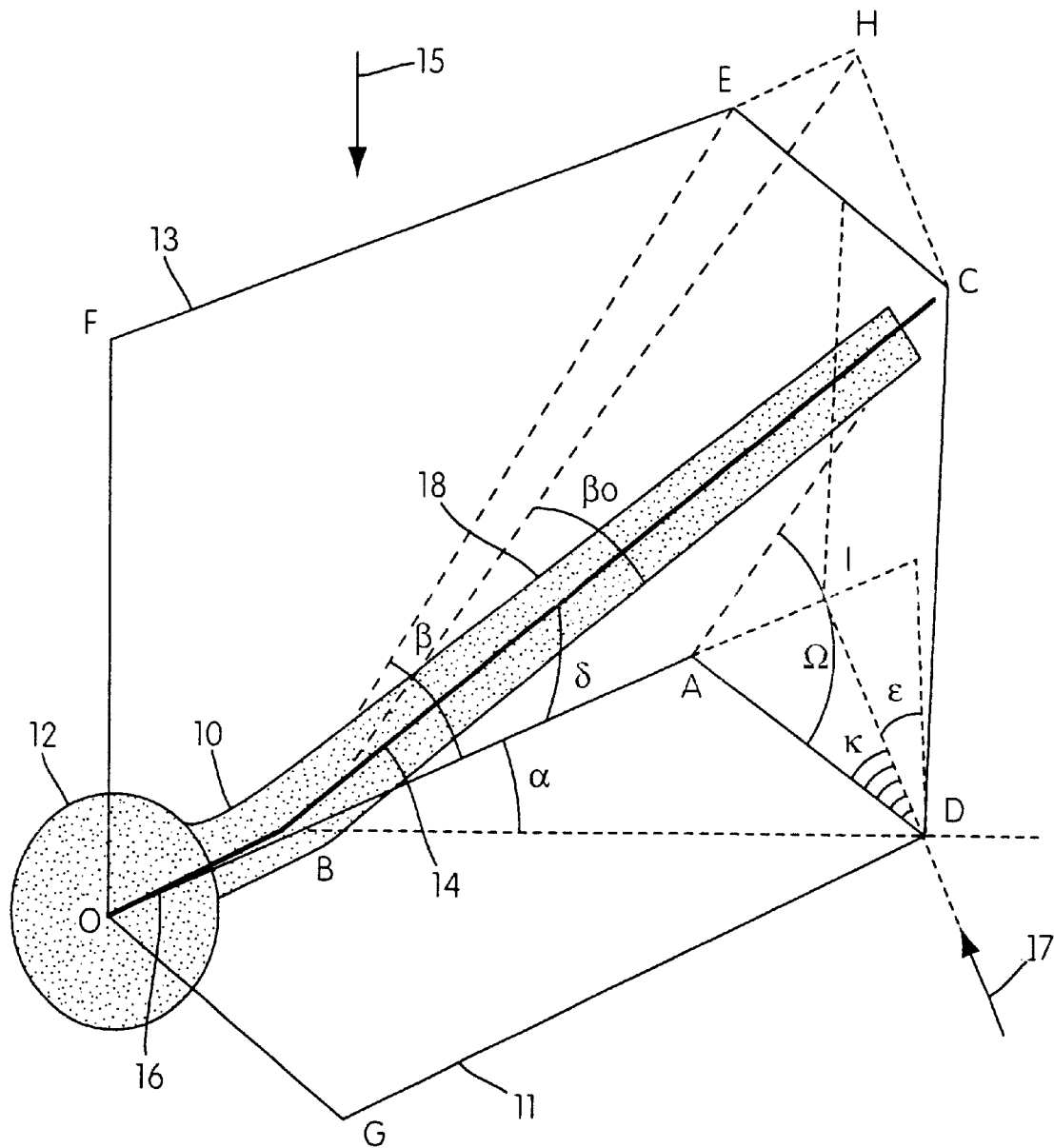
FIG. 1 schematically illustrates a femoral bone structure in perspective view, indicating symbols for mathematical calculation in accordance with prior art.

In order to accomplish a better determination of where to place fixating means, such as screws, pins, nails etc., on fractured bone parts, the present invention introduces a method specifically developed for the task. The method and arrangements herein disclosed for hip fractures are shown for purposes of illustration only, and are not limiting of the present invention. Hence, the method and means for perforation of bone structures according to the present invention can be used for any bone perforation, not only does related to hip fracture surgery.

The following description taken in conjunction with FIG. 1–9 is subject for a co-pending patent application, and FIG. 10–13 represent the present invention.

With the technique used in the present invention it is possible to achieve an accuracy of ±1.0 mm when attaching fixating screws in hip fracture surgery, and in addition determining the screw length, screw fixating angle, and dislocation degree of the fracture. A method used in connection with the present invention provides means for storing digitized radiographs from performed surgery and patient records in a database for quality checks and scientific research.

In radiographs of femoral neck fractures in accordance with prior art, the position of a pin or screw in relation to a construed femoral neck axis can be determined by measuring the distances from a discretionary point to a construed femoral neck axis, located at the same distance from the femoral head center in both the AP and lateral projections, to the pin or screw. The exact position is obtained if the following criteria are fulfilled:

1. The anteroposterior and lateral radioplates are parallel to the femoral neck axis and perpendicular to each other, and the anteroposterior radioplate is parallel to the femoral shaft axis.
2. The directions of the central X-ray beams in the anteroposterior and lateral projections are perpendicular to the femoral neck axis.
3. The degrees of magnification in the anteroposterior and lateral projections are equal.

A reversed method, i.e., it is determined where to place the pin or screw in the best possible way, is provided in connection with the present invention.

By using an image intensifier to adjust for the position of the femoral neck in space, the criteria nos. 1–3 can be fulfilled. This is time-consuming, however, and impracticable in routine examinations. In routine radiographs of internally fixed femoral neck fractures, the rotation of the hip varies in successive examinations and also in successive exposures, i.e. criteria nos. 1–3 above is not fulfilled. In order to determine the position of where to put pins/screws out off such radiographs, the rotated projections must be derotated to straight anterioposterior (AP) and lateral (Lat) projections. This is intuitively accomplished when a routine radiograph is interpreted, but this derotation is subjective and non-reproducible.

However, by determining the derotation angle omega ($\Omega$) the rotation of the hip can be compensated for in a reproducible way.

A femoral bone structure in perspective view marked up with symbols for mathematical calculation is schematically illustrated in FIG. 1. A method used for determining where fixating means have been placed after a performed surgery in hip fractures, derived from FIG. 1 is prior art, as stated above. Such a method was introduced and used by the inventor of the present invention in his study "Internal Fixation of Femoral Neck Fractures", Stockholm 1993, ISBN 91-628-0804-4. Nevertheless, the method has been used only for post-surgery quality checks and scientific statistics, see "Quality of Reduction and Cortical Screw Support in Femoral Neck Fractures", by Stig Lindequist and Hans Törnkvist, Journal of Orthopaedic Trauma, Vol. 9, No. 3, pp. 215–221, 1995 Raven Press Ltd, New York. A reversed method provided in connection with the present invention can be used in determining how and where to drill in a femoral bone fracture in order to facilitate healing of said fracture in a best possible way.

Despite the fact that the position of the fixation means in femoral neck fractures is considered to be of great importance for the outcome of a performed surgery, no other method of determining this position with a known degree of accuracy has been found in the literature.

It is a known fact that fixating means, as for example screws, are to be placed as adjacent to the femoral neck bone structure (the cortex) 10 as possible, and centered in the femoral head 12 so that a fractured neck 10 can bear relatively heavy loads. Loads of 1500 N is common. This should be considered along with elderly peoples deteriorated content of marrow inside the bone structure, which emphasis the importance of the screws being placed adjacent to the cortex.

"A Simple biplanar method of measuring femoral anteversion and neck-shaft angle" by Ogata K and Goldsand E M, J Bone Joint Surg (Am), 1979, 61:846–51, and "Radiographic measurements of the femoral anteversion, Acta Orthop Scand, 1983; 54: 141–46 by Herrlin and Ekelund, describes how the anteversion angle $\theta$ (not shown) and the neck-shaft angle $\delta$ can be calculated from the measured cerovicofemoral angles $\alpha$ and $\beta$, and the inclination angle $\epsilon$. According to their methods, the anteversion angle $\theta$ is obtained by an assumed derotation of the proximal end of the femur to zero degree of anteversion in the AP and Lat projections. This derotation takes place along the femoral shaft axis 14 and with the lateral radiograph plate positioned along the femoral shaft. However, an assumed derotation of the proximal end of the femur to zero degree of anteversion in the AP and Lat projections can also take place along the femoral neck axis 16. This angle of derotation around the femoral neck axis 16 is defined as Ω. The relation between the rotation angle of the femoral neck Ω, the projected cerovicofemoral angles α and β, the inclination angle ε, the deviation angle κ and the true femoral neck-shaft angle δ can be expressed as follows:

$$\sin \Omega = CD/AC = HI/AC = \tan \beta o^*(AB+AI)/\tan \delta^* AB \tan \kappa = AI/AD$$

and $$\tan \alpha = AD/AB,$$

therefore $$\sin \Omega = \tan \beta o^*(AB+\tan \alpha^* \tan \kappa^* AB)/\tan \delta^* AB$$

$$\sin \Omega = \tan \beta o^*(1+\tan \alpha^* \tan \kappa)/\tan \delta$$

$$\tan \delta = AC/AB \text{ and } \cos \Omega = AD/AC,$$

therefore $$\tan \Omega = \tan \beta o^* \tan \kappa + \tan \beta o/\tan \alpha$$

where κ is the angle of deviation of a central X-ray beam from a direction perpendicular to the femoral neck axis in the lateral projection, and where ε=δ±κ

If a derotation by Ω degrees of the femoral neck 10 is assumed to occur, a pin placed along the femoral neck axis will also rotate Ω degrees. If the co-ordinates for the pin position in the digitized radiographs are to be X and Y, a matrix for transformation of co-ordinates in a right-angled co-ordinate system, $$X' = Y^* \sin \Omega + X^* \cos \Omega;$$

$$Y' = Y^* \cos \Omega$$

will give the corrected co-ordinates X' and Y' for a pin/screw position in the straight AP and Lat projections.

FIG. 1 further illustrates distances and angles OADG: Parallel to the film plane 11 in the AP projection 15; OAEF: Parallel to the film plane 13 in the lateral projection 17; OB: Central axis of the femoral neck 10; BC: Central axis of the femoral shaft 18; α: Cervicofemoral angel in the AP projection 15; β: Cervicofemoral angle in the lateral projection 17 when the central X-ray beams are perpendicular to the femoral neck axis 16; βo: Cervico-femoral angle in the lateral projection 17 when the central X-ray beams are not perpendicular to the femoral neck axis 10; ε: The angle of inclination of the central X-ray beams in the lateral projection 17; κ: The angle of deviation of the central X-ray beams in the lateral projection 17 from a direction perpendicular to the femoral neck axis 10; δ: True femoral neck-shaft angles and Ω: Femoral neck rotation angle.

Figure 2:
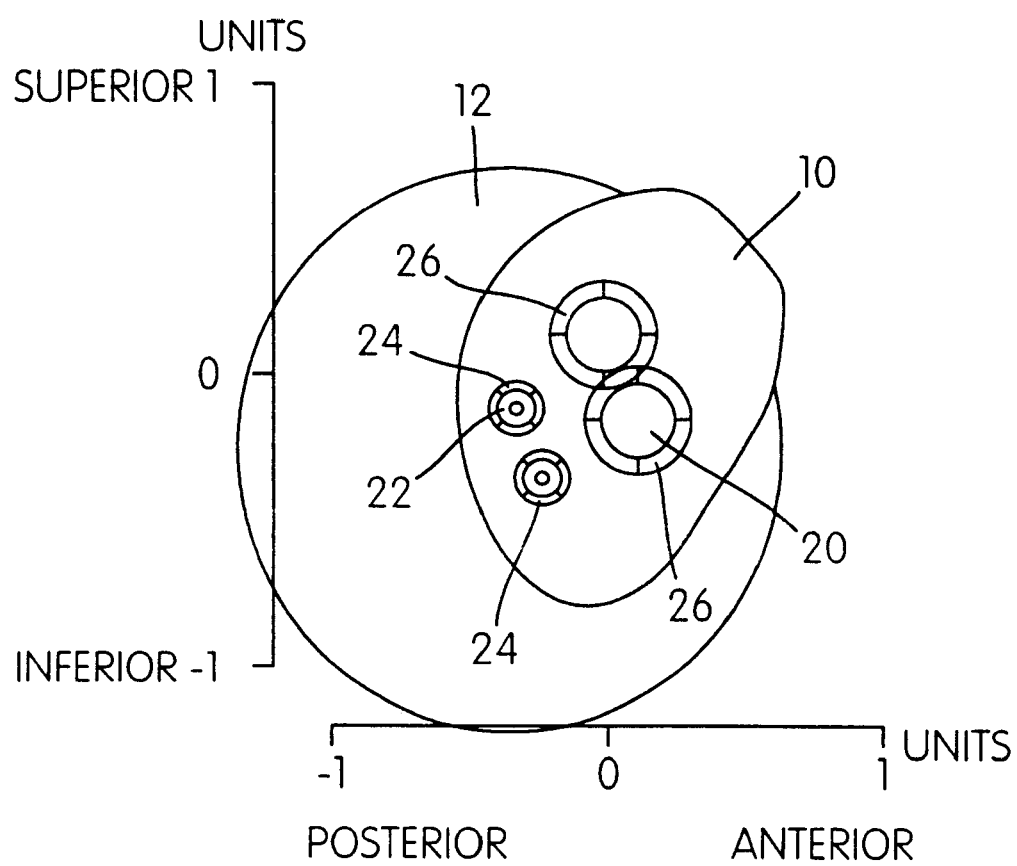
FIG. 2 illustrates a cross-section of a dislocated hip fracture showing symbols for fixating means according to the present invention.
Figure 3:
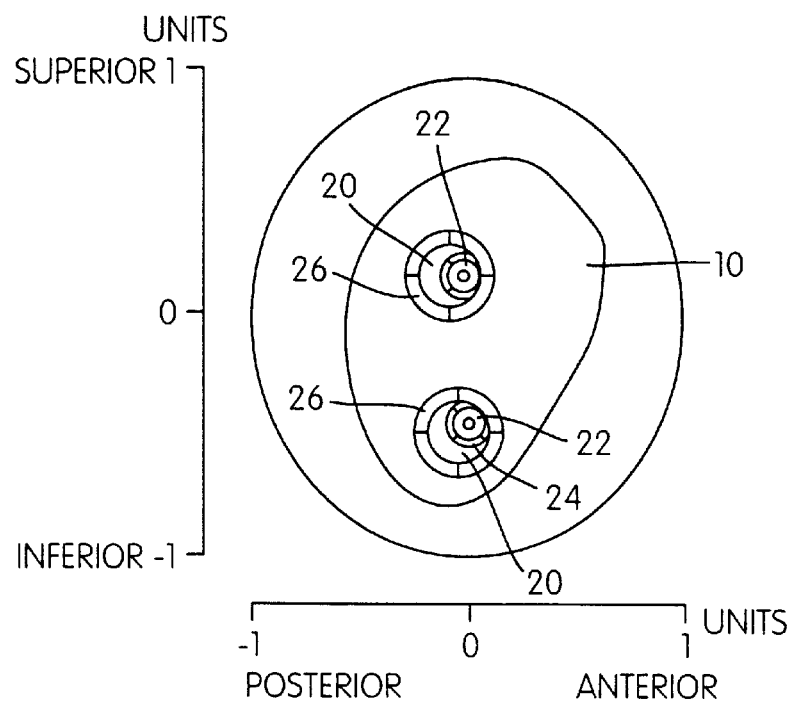
FIG. 3 illustrates a cross-section of a non-dislocated hip fracture displaying symbols for fixating means according to the present invention.

The transformed co-ordinates X' and Y' in the femoral head 12 are plotted in a Cartesian co-ordinate system and circumscribed by a circle with the center placed at the origin of the co-ordinate system, and with the radius equal to that of the femoral head 12 at the measuring point. The obtained graph represents a cross-section of the femoral head at the level of the measuring point, as illustrated in FIG. 2 and FIG. 3 described below.

For the femoral neck 10, the transformed co-ordinates X' and Y' are plotted in a co-ordinate system and circumscribed by cross-section graphs of the femoral neck 10.

If series of radiographs are to be compared to each other, all measured distances are converted from mm to units of measurement by dividing the distance by the diameter of the femoral head 12 on the film in question. The values for pin co-ordinates are expressed as fractions of the femoral head diameter.

Provided with the present invention, a known method named PINTRACE™ has been adapted and developed, to suggest screw positions, in said femoral neck axis 10 and said femoral shaft axis 14 in the AP and Lat radiographs instead of only analyzing already applied screws. The known older method PINTRACE™ was developed by the same inventor as for the present invention and referred to in his thesis "Internal Fixation of Femoral Neck Fractures", Stockholm 1993, ISBN 91-628-0804-4.

In the original older method PINTRACE™, the positions of inserted fixating pins/screws are calculated and presented in constructed cross-sections of the femoral neck 10 and head 12. An entirely new PINTRACE 2.0™ method was developed. In fact, the common part between the old known PINTRACE™ and the new PINTRACE 2.0™ method is that the configuration according to FIG. 1 is provided in order to make necessary calculations possible. The old PINTRACE™ method is a sub-method to the method provided together with the present invention where the shape of the femoral neck 10 and head 12 are determined, constructed and displayed on, for example, a computer screen as empty cross-section graphs. This allows a surgeon to place symbols for fixating pins/screws, or use displayed predefined positions for such symbols. It should be appreciated that placing symbols is a dynamic task, which varies among patients, considering the importance of placing pins/screws as adjacent to the cortex as possible. Positions of provided symbols are transferred to the digitized AP and Lat radiographs and overlaid on these in form of colored lines of varying thickness.

To assist a user in detecting incorrect measurements of the femoral neck radii, (PINTRACE 2.0™), according to the present invention, uses a standard neck/head ratio (AP view=0.70, lateral view=0.57: "The proximal end of the femur" thesis by Backman, Karolinska Institutet, Stockholm 1957, and "Anatomy of the Femoral Neck and Head with comparative data from Caucasians and Hong Kong Chinese, Hoaglund and Low, Clin.Orthop 152: 10–16, 1980) for a preview calculation of the femoral neck AP and lateral radii. The user can change the calculated standard radii if they differ from the measured radii on the film in question.

FIG. 2 illustrates a cross-section of a dislocated hip fracture displaying symbols for fixating means, here screws indicated by broken lines and filled circles, provided in connection with the present invention.

The cross-section view in FIG. 2 of caput 12 (femoral head) and collum femoris 10 (femoral neck) shows a dislocated hip fracture with two screws attached. Filled black circles 20 represent the position of said screws in collum femoris 10, and filled white circles represent the position of screws in caput 12. Adjacent circles 24, 26 indicate a specific degree of uncertainty for marked up screw positions.

Further, FIG. 3 illustrates a cross section of a non-dislocated hip fracture displaying symbols for fixating means, here screws indicated by broken lines and filled circles, according to the present invention.

The cross-section view in FIG. 3 of caput 12 and collum femoris 10 shows a non-dislocated hip fracture with two screws attached. Filled black circles 20 represent the position of said screws in collum femoris 10, and filled white circles represent the position of screws in caput 12. Adjacent circles 24, 26 indicate a specific degree of uncertainty for marked up screw positions.

Figure 4:
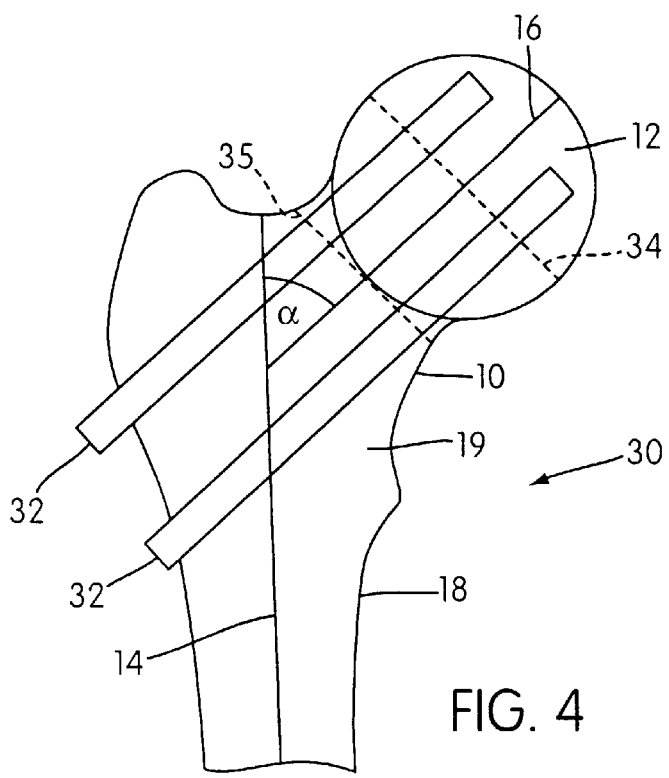
FIG. 4 illustrates a femoral bone structure from its anteroposterior projection with marked screw positions according to the present invention.
Figure 5:
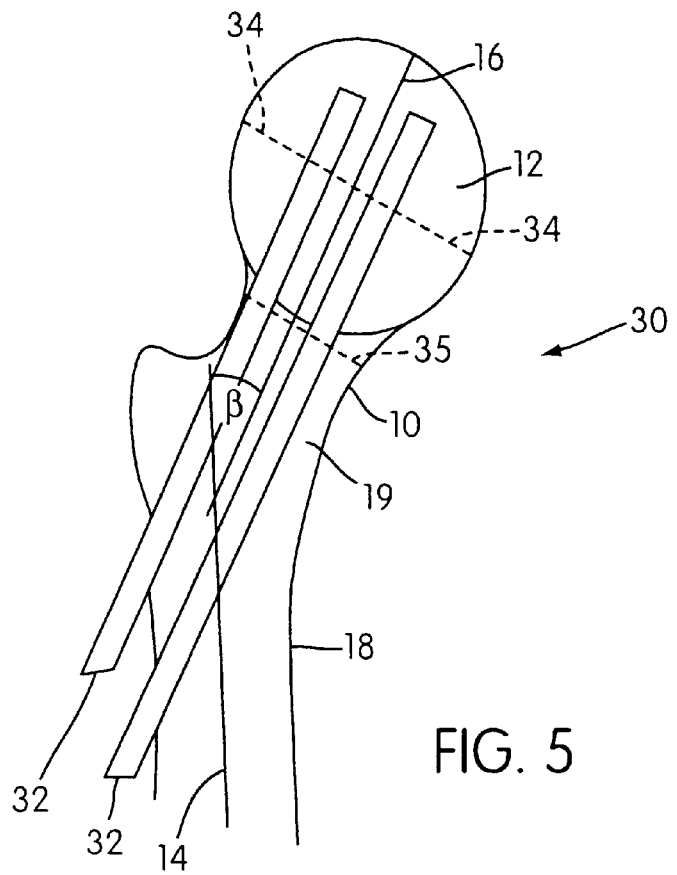
FIG. 5 illustrates a femoral bone structure from its lateral projection with marked screw positions according to the present invention.

Now referring to FIG. 4 and FIG. 5.

FIG. 4 illustrates a femoral bone structure 30 from its anteroposterior projection 15 with two marked screws.

FIG. 5 illustrates a femoral bone structure 30 from its lateral projection 17 with two marked screws 32.

In the AP and Lat radiograph projections 15, 17 the central axes 14, 16 of the femoral neck 10 and shaft 18 are marked and the femoral neck-angles α and β are measured. The distance from the femoral neck axis 16 to a marker which indicates where to position a screw 32, when surgery is performed, at one measuring points in the Lat view 17 is taken to represent the X co-ordinate and the distance in the AP view 15 the Y co-ordinate for the pin. Angles as shown in FIG. 1, FIG. 4 and FIG. 5 are used to place the femoral bone structure 30 in space, thus finally indicating the direction for insertion of screws 32.

Co-ordinates in the inferior or posterior halves of the femoral head 12 and neck 10 are assigned negative values, see FIG. 2 and FIG. 3.

For the femoral neck 10, the point of intersection of the femoral head sphere and the femoral neck axis 16 is used as measuring point. The diameters 34, 35, indicated by broken lines in FIGS. 4 and 5, of the femoral head 12 and neck 10 are determined at the measuring points in both the AP and Lat projections 15, 17.

Since magnification factors in the AP and Lat projections often differ, all measured distances are adjusted by calculating the ratio of the greatest and the smallest femoral head diameter and then multiplying the distances in the projection with the smallest diameter by the ratio.

A method for determining, in three dimensions, where to position fixating means in a hip fracture by pre-surgery analysis of at least one anteroposterior and one lateral digitized radiograph of said fracture, is provided in connection with the present invention. It comprises the following steps:

determining a construed femoral shaft axis 14 out off said graphs from at least two midpoints on said shaft axis and drawing a line through said midpoints;

determining a construed femoral neck axis 16 from at least two midpoints on said neck axis and drawing a line through said midpoints;

determining femoral neck angles α, β determining a femoral head diameter 34 out off said graphs by placing a circle over the perimeter of the femoral head 12;

scaling and rotating said radiographs to a predefined size and position, using an angle between the femoral shaft and an Y-axis in said digitized radiographs, and said diameter 34 of the femoral head 12;

determining the distance from said neck axis 16 and the center of said femoral head, representing a remaining displacement of the hip fracture which is implicitly known from said diameter 34;

measuring the height of the medial cortex 19 out off the anteroposterior graph;

displaying said femoral neck angles α, β;

displaying cross-sections (FIG. 2 and FIG. 3) of the femoral head 12 and neck 10 with a predetermined degree of accuracy;

rotating said cross-sections of the femoral head 12 and neck 10 in order to determine a degree of derotation of the hip, imposed by the fracture, displaying the degree Ω of hip rotation in said anteroposterior and lateral radiographs; and in one embodiment using said steps in an arrangement in order to determine a position, in three dimensions for attachment of said fixating means 32 and to pre-adjust a tool to work in said position.

Femoral neck-/shaft-angels α, β are preferably displayed both as lines and as numerical values in said digitized graphs, said lines are automatically re-drawn if the value is changed.

Lines are possible to determine with two midpoints, but it should be understood that a more exact line is obtained by drawing a regression line from at least three midpoints on said axes.

Symbols 20 for said fixating means are placed within the cross-section of the femoral neck 10 and a warning function is activated if said fixating means are placed outside of the femoral neck 10 in said digitized radiographs.

Fixating means 32 for attachment are automatically displayed in said graphs, through graphical means known per se, with relation to made measurements. Also, it is possible to put down symbols 20 for fixating means 32 in the digitized radiographs.

In accordance with the present invention, radiographs are analyzed before any surgical treatment, and measured and computed values can be applied as control input to an arrangement 40 which accomplishes insertion guides, holes for example, for bone fracture fixating means 32, said arrangement 40 being described below.

Figure 6:
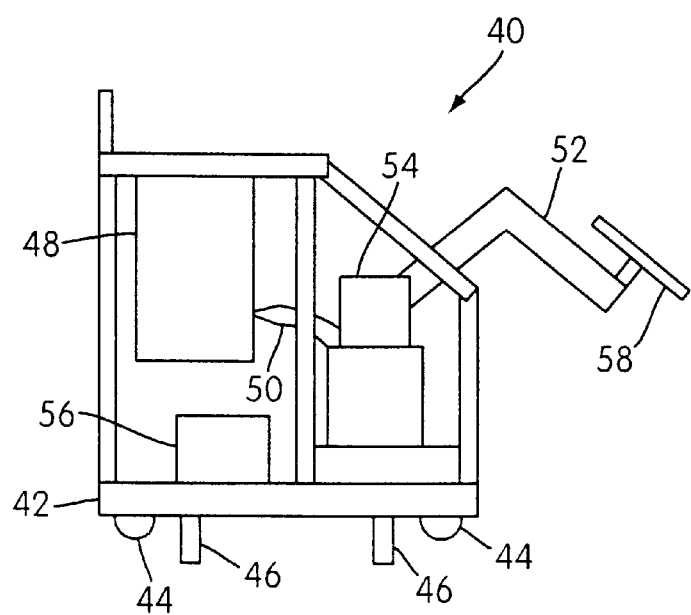
FIG. 6 illustrates a side view elevation of an arrangement according to the present invention.
Figure 7:
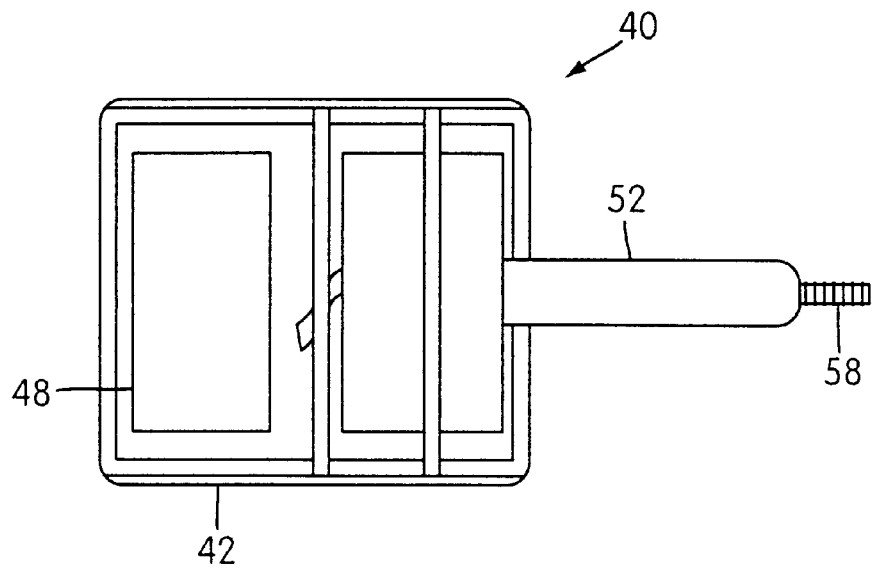
FIG. 7 illustrates a top plan view of an arrangement according to the present invention.
Figure 8:
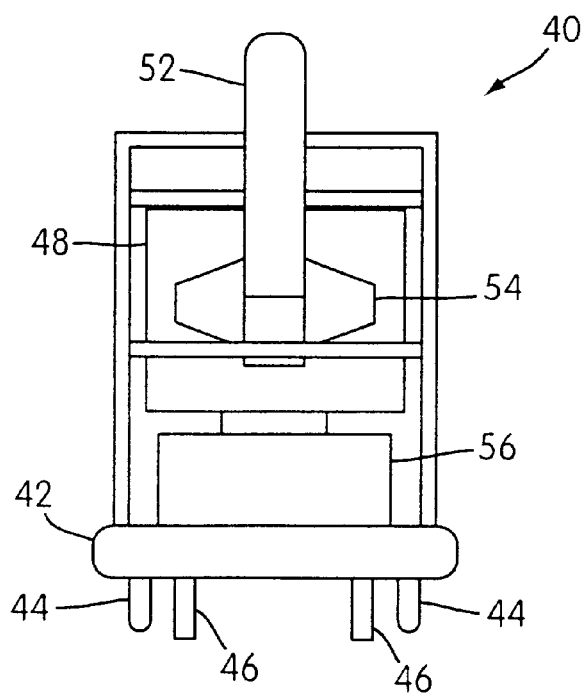
FIG. 8 illustrates a front view elevation of an arrangement according to the present invention.

FIG. 6 illustrates a side view elevation of an arrangement 40 provided in connection with the present invention;

FIG. 7 illustrates a top plan view of an arrangement in accordance with FIG. 7; and FIG. 8 illustrates a front view elevation of an arrangement 40 in accordance with FIGS. 6 and 7.

The arrangement 40 according to the embodiment schematically shown in FIGS. 6–8 is a robot on a mobile stand 42 attached with wheels 44 and adjustable feet such as bars, poles 46 or the like for stabilization when ever needed. Further equipment attached, is a control box 48 with a cable link 50 connected to an articulated robot arm 52 with servo or stepper motors 54. A transformer 56 distributes power. The control box 48 is adapted to be connected to peripheral equipment such as a computer with I/O ports for control and communication, a display device, a printer, scanner, frame grabber, and other known computer equipment.

Also, attached on the robot arm 52 is a tool holder 58, for example, used to hold a drilling-machine.

It is comprised in the present invention that said control box 48 for controlling the robot contains hardware devices, firmware devices and software controlled by a processor, each device known per se, but forming an unique entity for applications according to the present invention. Although, in this preferred embodiment of the invention, only one measurement means is described for performing measurements, it is appreciated that measurement means/function can be composed of multiple means, or integrated into one or more means/function as described below.

Thus, in one preferred embodiment comprising means and/or functions, such as:

measurement means or function accomplishing measurement of the femoral shaft axis 14 out off said graphs from at least two midpoints on said shaft axis, calculating and drawing a line through said midpoints. Further, the device or function measures a construed femoral neck axis 16 from at least two midpoints on said neck axis, 16, calculating and drawing a line through said midpoints. The femoral neck angles α, β are determined. Still further, it measures the height of the cortex 19 out off said anteroposterior graph. Also, the means measures, calculates and determines the femoral head diameter 34 out off said graphs by placing a circle over the perimeter of the femoral head 12, and measures, computes or determines the distance from the femoral neck axis 16 to the center of said femoral head 12, representing a remaining displacement of the fracture, which is implicitly known from said femoral head diameter 34, whereby the means measures, calculates and determines the femoral neck diameter 35 out off said graphs by drawing a line, perpendicular to the femoral neck axis, at the intersection of the femoral head sphere and the central femoral neck axis 16;

a scaling function scaling and rotating said radiographs to a predefined size and position, using an angle between the femoral shaft and an Y-axis in a display, displaying co-ordinate axes together with said digitized radiographs, and said femoral head diameter 34;

a display device for displaying data of interest to hip fracture surgery e.g. digitized radiographs, neck angles α, hip rotation Ω, cross-sections (FIGS. 2 and 3), computed figures, lines 16, 14, etc.

a function providing displays of said cross-sections of said femoral head 12 and femoral neck 10;

a driver for rotating said cross-sections of the femoral head 12 and neck 10 in order to determine a degree of hip derotation between said head and neck, imposed by the fracture; said means providing control input to a robot with stand means 46 for said robot, tool means on said robot for working in a direction given by said control input, and distortion correcting means (not shown) compensating for x-ray distortion.

Femoral neck angles α,β are displayed by said display as lines and numerical values in said digitized graphs. The lines are automatically re-drawn, preferably controlled through software and/or graphic means, if the value is changed.

Symbols 20 for said fixating means are placed within the cross-section of the femoral neck and displayed by said display.

It is included a device or function that activates a warning function if fixating means 32 are placed outside the femoral neck in said digitized radiographs.

Further, it is included that fixating means for attachment are automatically displayed in said digitized radiographs with relation to made measurements, by software.

Means, such as graphic drivers, can be provided for putting down symbols for fixating means 20, 32 in the digitized radiographs of the present invention.

The method as herein described is preferably applied to control the robot in using its tool to work in the right direction, and prepare for insertion of fixating means such as screws, pins, nails, etc.

The distortion compensating means according to the present invention is described below.

Figure 9:
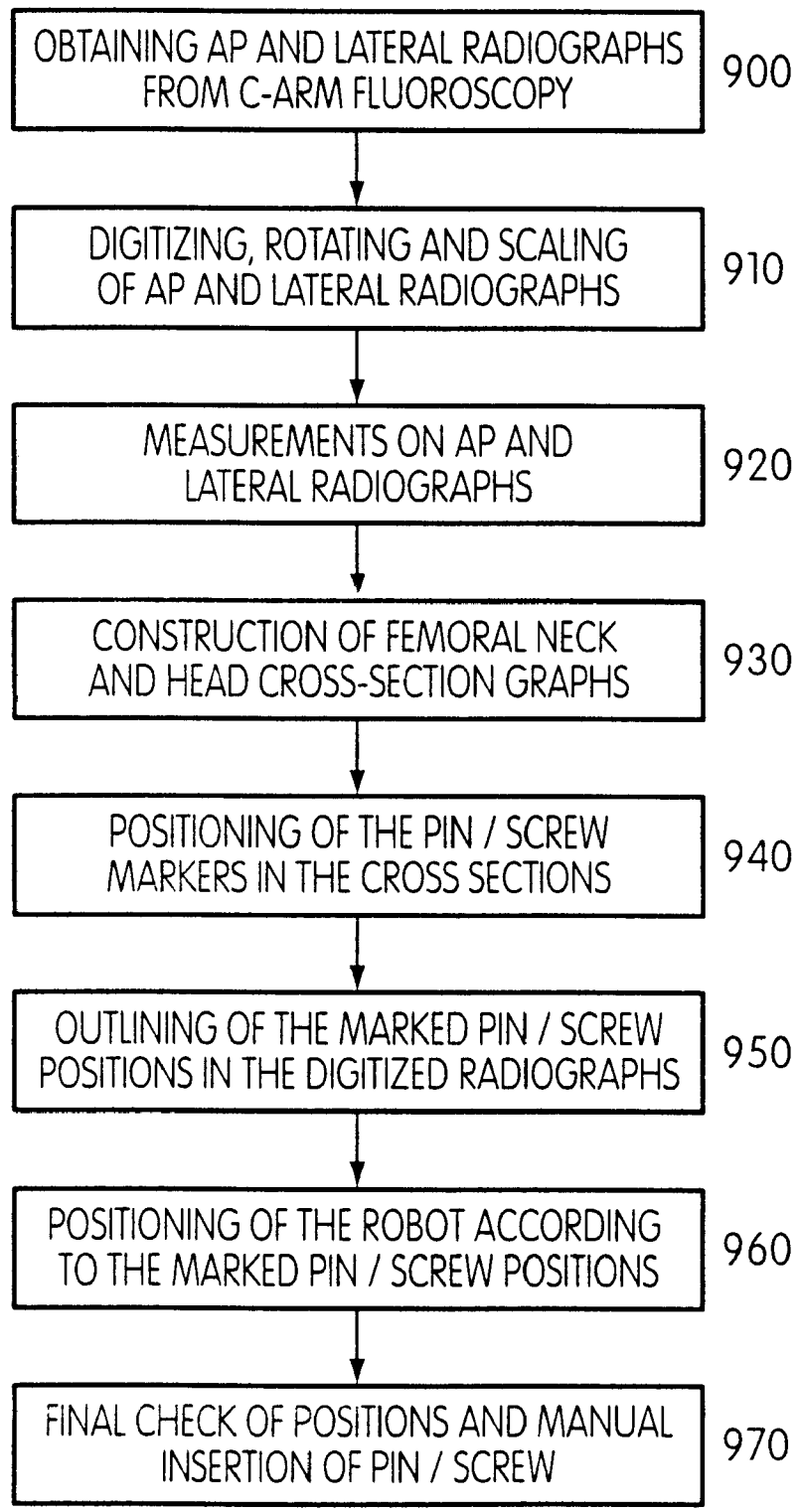
FIG. 9 illustrates a flow chart depicting steps taken in a method of the present invention.

Now referring to FIG. 9, which illustrates a flow chart depicting steps 900 to 980, taken in the method of the present invention, which is applied as control information to an arrangement.

At step 900 AP and Lat radiographs from C-arm fluoroscopy are obtained. The radiographs are digitized, rotated and scaled 910, by drivers for that purpose, followed by performing 920 necessary measurement operations, with means or functions described above, on the radiographs of a hip fracture.

Made measurements are resulting in construction 930, through a software, of femoral neck and head cross-section graphs, which are displayed on a screen. Displayed cross-sections are marked 940 with pin/screw markers, which are changeable through software. An outlining 950 of the marked pin/screw positions in the digitized radiographs is thus performed.

The steps 900–950 are applied to position 960 a robot to drill in said positions. This is followed up by a final check of determined positions. Eventually, during surgery, a surgeon manually inserts 980 pins/screws.

Accordingly it should be understood that the PINTRACE 2.0™ method or like methods are adapted to the method described in accordance with the flow chart.

Henceforth the present invention is described in conjunction with FIG. 10–13. The following description is had to a preferred embodiment of the present invention, but the invention is not limited to this specific embodiment.

Figure 10:
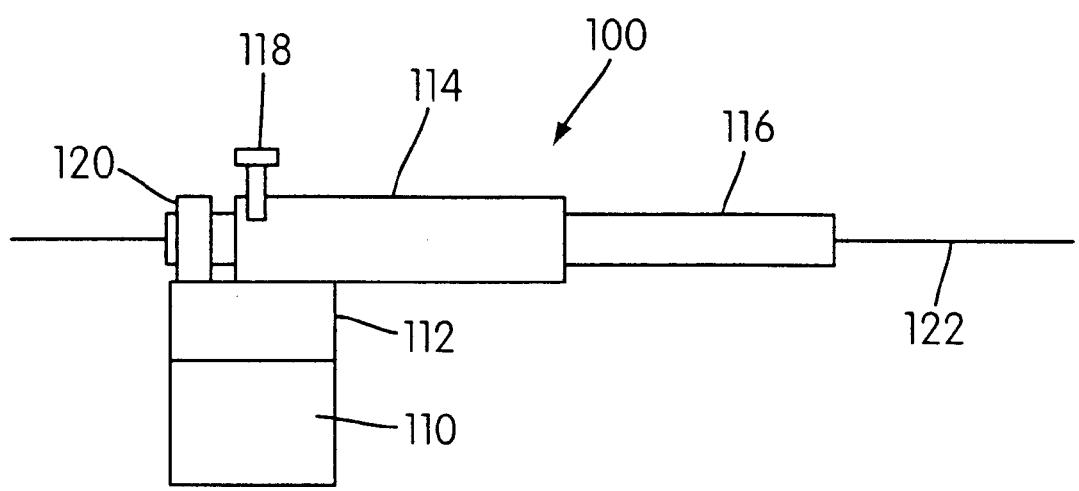
FIG. 10 illustrates a side view elevation of a casing with a tool holder on a support according to the present invention.
Figure 11:
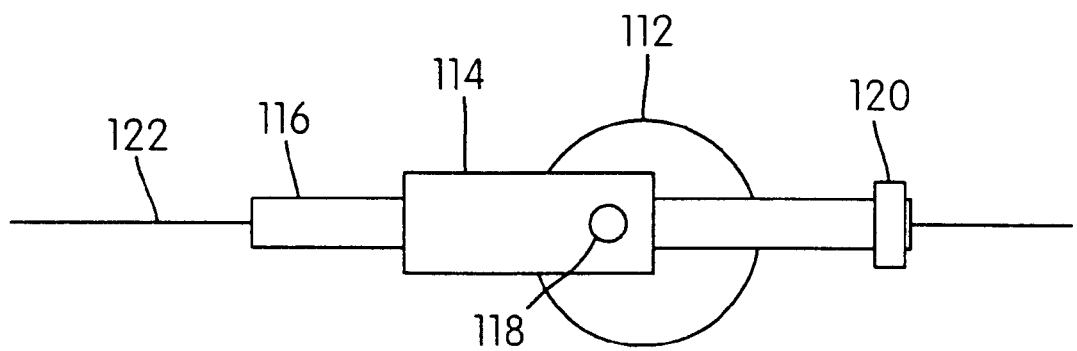
FIG. 11 illustrates a top plan view of a casing with a tool holder in accordance with FIG. 10.

FIG. 10 illustrates a side view elevation of a casing with a tool holder on a support according to the present invention; and FIG. 11 illustrates a top plan view of a casing with a tool holder in accordance with FIG. 10.

The arrangement 100 with a tool holder or drill guide system as depicted in FIG. 10 and 11 comprises a support 110 to be mounted on a machine 40, like a robot with an articulated arm 52. It further comprises a means of attachment 112 for support 110 and an outer casing 114 with a slide-able inner casing 116 acting as a so called end effector holder or tool holder with a stop screw 118 for locking of the inner casing 114. A flanch 120, for forming of a stop position for the inner casing, is provided. Finally an X-ray marker pin 122 is hold by the inner casing. The marker 122 can as well be changed to another end effector such as a tool, for example, a tool for drilling, screwing, pinning, milling, grinding, threading etc, or even machines for the same purposes could be attached to the inner casing 116.

In a preferred embodiment, the support 112 is turnable and lock-able (not shown).

Figure 12:
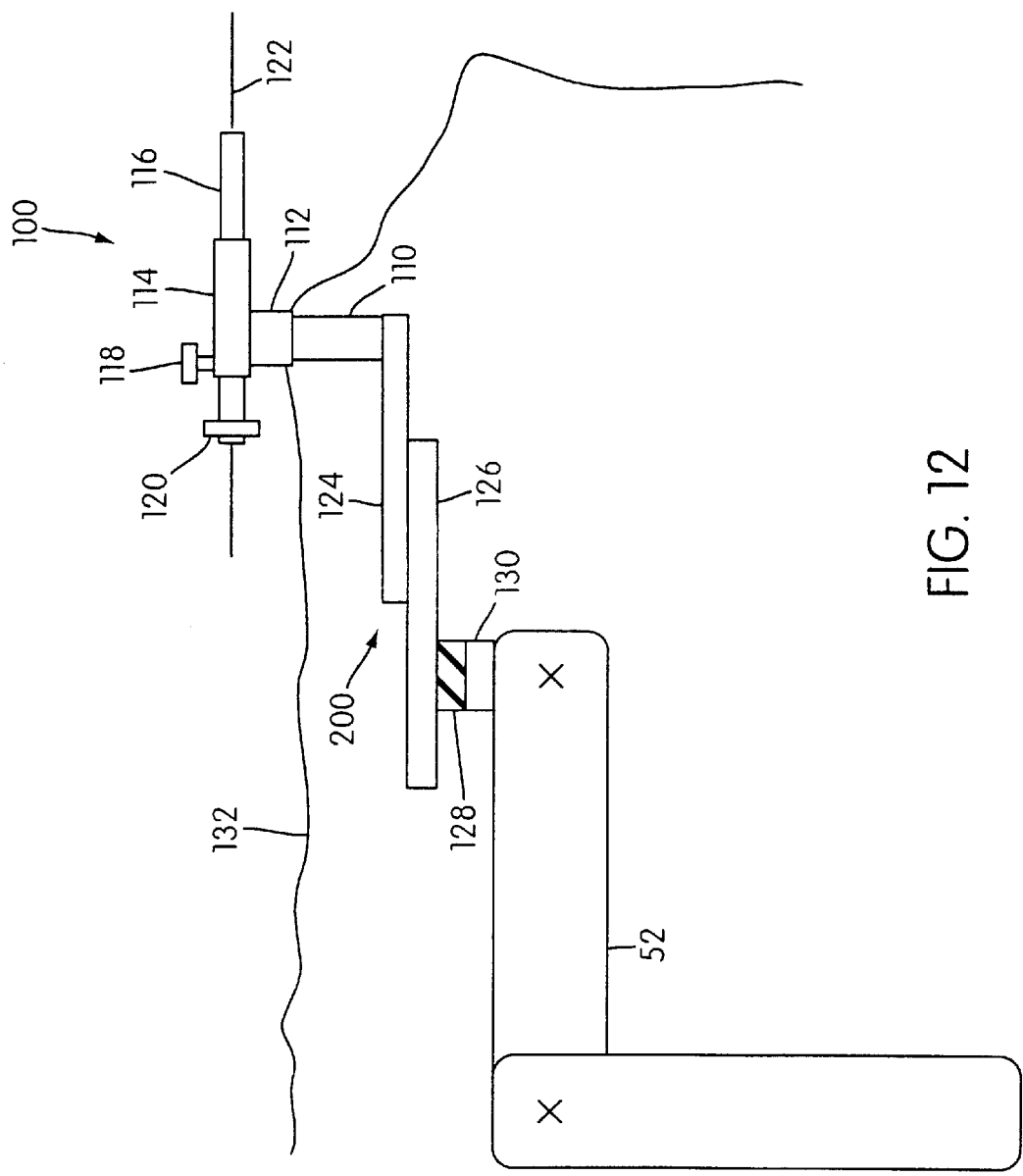
FIG. 12 illustrates a side view elevation of a casing with a tool holder and support mounted on a robot arm according to the present invention.

Now referring to FIG. 12 which illustrates the arrangement according to FIGS. 10 and 11 attached to an articulated robot-arm 52. The arrangement comprises the same components as in the two previous figures and a sliding arrangement 200 with upper 124 and lower 126 slide-able plates. The lower slide-able plate 126 is attached to an electrically isolating plate 128, and working flanch 130 (platform 130) articulated attached to the robot-arm 52.

Sliding plates 124, 126 mounted on a robots working flanch 130 makes it possible to move a part of the arrangement 100, manually or by electric means in a forward —backward direction. An electronic distance measuring apparatus is attached to the sliding arrangement 200 and provides input to the robot about the distances the sliding device has moved.

The casing 114 is possibly a metallic cylinder and attached to the support 112. Another casing 116 formed as a metallic cylinder fits into the first cylinder 114. It is provided with a central hole through which pins or drills can be introduced. The inner cylinder 116 is available with different diameters of the central hole through which different end effectors such as drills, screws, pins etc can be introduced.

A small steel pin 122 with radiographic markings for each 25 mm at one end is introduced through the central hole and serves as a measurement guide.

Also depicted in FIG. 12 is a sterilized cloth 132 for anti bacterial protection during preparations for surgery.

Figure 13:
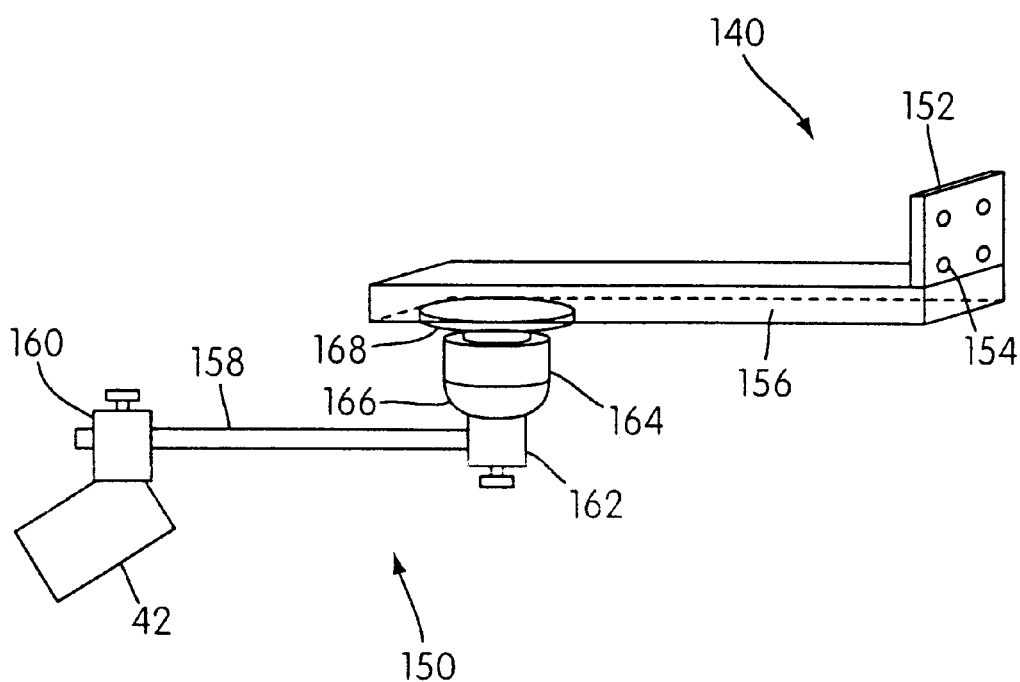
FIG. 13 illustrates a positioning determining means mounted on a support and attached to a robot fundament or stand according to the present invention.

Now referring to FIG. 13 which shows a positioning determining arrangement 140 mounted on a support 150 and attached to a support connected to the robot fundament or stand 42 according to the present invention.

X-ray distortion is compensated for with a new inventive method and an arrangement 140, 150 for that purpose.

X-ray distortion such as magnification arises from a diverging X-ray beam as it is emitted from an X-ray tube towards a radioplate. Hence by having a reference at a predetermined distance from the tube a magnification factor would be gained by the ratio of the distance measured on a radioplate with the known distance of the reference.

The arrangement comprises, in a preferred embodiment, a plexiglass plate 152 with four lead balls 154 attached and placed in a square pattern. While trans-illuminating in the AP and Lat projections in parallel with the ball pattern, two balls 154 are adjusted to be placed in the center of the radiation field so that they cover each other entirely. Thus, through measuring the distance between the two balls that are uncovered, an absolute measure of the distortion is determined (the magnification ratio) provided that a predetermined distance between the radiation tube and the plexiglass 152 plate is upheld. This distance corresponds to the working distance when distance determinations are made. A calculation in percentage to adjust the robot arm is finally applied.

Depicted in FIG. 13 is an open plexiglass box 140 with two plates 154, 156 attached orthogonal to each other. Plate 154, in a vertical position in FIG. 13, provided with four X-ray opaque balls in a square pattern. The plates 154, 156 are mounted on a support 150, which is attached to a fundament 42 for the robot. Four means of attachment are making up the support 150. A first means 158, here a rod, is mounted on a frame 160 of the robot fundament 42, which is movable back and forth in relation to the frame 160. A second means 162 is movable around the rod 158, and attached to the rod 158. A third means 164 is attached to an axis 166 which makes it movable in a vertical direction to said means 164. Finally, the fourth means 168 is movable in relation to said third means 164 horizontal and slide-able in all directions possibly in 360 degrees if necessary.

Said plates 152, 156 are of a material substantially transparent to X-ray radiation and provided with 4 round elements in a square configuration. The round elements are made of X-ray opaque material such as tantalum, lead, steal etc. The support 150 is movable in three dimensions so it can be placed in front of robot 40 end effector and, after measuring, retracted so it does not disturbe the movement of a robot arm 52.

Specific steps 1)–3) are provided for control of position determining etc in accordance with the present invention, seth forth below:

1) A computer program designed to calculate the magnification factor from measurements on the measuring template (position determining arrangement).
2) A computer program designed to calculate the desired movement of the robot arm from input measurements through i) the position of the Alignment system, ii) the position of the Marking pin and iii) the marked position for the drill/screw/pin in the bone.
3) A computer program for checking the final robot position.

Henceforth, a method used in the present invention is described.

A) Activate the robot arm and move to a defined start position with, for example for drilling, the arrangement for marking 100 pointing forward and the marking pin 122 put in place and extending, for example, 50 mm. The robot is assigned a first start tool Position, i.e. the robot adapts its co-ordinate system so that each movement is carried out around the tip of the marking pin 122. Said measuring template 140 is placed in front of the drill guide 100. Place the measuring template vertical to the floor and adjust it so that the marking pin 122 hits each round element 154 when the robot moves a specified distance in a square pattern.

B) Placing of the measuring template 140 adjacent to the part of a body where the drilling/screwing is intended. A movable X-ray machine (C-arm) is placed and adjusted so that, when radiographs are taken, two out of the four round elements 154 cover each other in the two orthogonal planes (AP and Lat projection). The position for the two covered round elements represent a starting position for the robot. Said two radiographs are digitized and fed into a computer and the distances between the two uncovered round elements, representing the magnification factor, is calculated and displayed by a computer program. The magnification factor relates to the movement of the robot arm.

C) Said thin steel-pin 122 (the marking pin) with radiographic markings for 25 mm on one end introduced through the central hole in the second cylinder so it protrudes 50 mm. By advancing the sliding arrangement 200 the marking pin 122 penetrates through the skin and muscles to a position close to the bone which is to be drilled. Distances the sliding device has to move are measured manually or electronically and fed into a robot 40 computer program. Now providing the robot a second tool position, start tool position two, according to the distance the sliding device has moved. Now letting the arm 52 move around this second position even if the pin and second cylinder is removed, meaning that all robot movements can take place outside the patients body, but the center of movements will still be close to the bone inside the patients body.

D) Two radiographs (AP and Lat) are taken and digitized, and fed into a computer. The position of the marking steel pin 122, and the length of the 25 mm marking, are measured on the digitized radiographs. A scale factor for this position is calculated.

E) A desired position for the drill/pin/screw in the bone is marked on the digitized radiographs. The computer program now compares the desired position for the drill/pin/screw in the bone with the actual position for the marking pin. After making corrections for magnification (B) and Scale (D) the computer calculates the distances and angles the robot has to move in order to align the marking pin with the desired drill/pin/screw position in the bone. These distances and angles are fed into the robot computer and the robot repositions itself accordingly.

F) After the robot 40 has moved into the new position, the marking pin 122 and the second cylinder 116 is changed to similar devices, suitable for drilling, screwing, pinning etc. A chosen end effector is advanced by means of the sliding arrangement 200 so that it enters through the skin and muscles to a position close to the bone. At this, AP and Lat radiographs are taken and digitized. A computer program performs a checking procedure by marking and outlining the direction and position of the end effector (pin/screw/drill) and comparing it with the marked desired pin/screw drill position. If the trajectory of the end effector deviates more than a specified distance from the marked desired position, the positioning procedure is redone from the present position. This will considerably reduce the distances the robot has to move and therefore reduce the positioning errors.

G) When the end effector is optimally positioned, the surgeon manually introduces pins/screws or drills through second cylinders 116 with central holes in different sizes. A drilling machine can also be fixed to the sliding device and automatically introduce the end effectors. To ensure stability and safety, the robot arm is locked during drilling procedures, thus creating a stable platform for these procedures.

It is thus believed that the operation and construction of the present invention will be apparent from the foregoing description. While the method and arrangements shown or described have been characterized as being preferred, it will be obvious that various changes and modifications may be made therein without departing from the spirit and scope of the invention as defined in the following claims.

What is claimed is:

1. A position determining arrangement used for finding directions for perforation in bone structure surgery, attachable to a machine with a movable arm, wherein the position determining arrangement is provided with a first plate and a second plate, said first and second plates being substantially transparent to X-ray radiation in an orthogonal direction, and mounted in an orthogonal configuration, said first plate being provided with four round elements, said second plate being mounted on a turnable and tiltable support for attachment to said machine or initially attached, whereby an X-ray magnification factor relating to two orthogonal X-ray radiographs, comprising the four round elements, taken of bone structure is determined when two of said four round elements cover each other in both radiographs, said magnification factor being determined by a distance between two uncovered round elements of said four round elements and dependent on movement of said movable arm.

2. An arrangement according to claim 1, wherein said turnable support is mountable to a movable frame of said machine, whereby the turnable support is positionable in front of an arrangement for marking of directions and holding of tools for perforation on said machine.

3. An arrangement according to claim 1, wherein said four round elements are opaque to X-ray radiation.

4. An arrangement according to claim 3, wherein said four round elements are made out of a material opaque to X-ray radiation, said material including at least one of tantalum, lead, and steel alloys thereof.

5. An arrangement according to claim 1, wherein said four round elements are placed in a square configuration on said first plate.

6. An arrangement according to claim 1, wherein said four round elements are provided only on said first plate.

7. An arrangement according to claim 1, wherein said four round elements are not provided on said second plate.

8. An arrangement according to claim 1, wherein said first plate is provided with no more than four of said round elements.

9. A position determining arrangement used for finding directions for perforation in bone structure surgery, attachable to a machine with a movable arm, wherein the position determining arrangement is provided with a first plate and a second plate, both plates being substantially transparent to X-ray radiation in an orthogonal direction, and mounted in an orthogonal configuration, said first plate consisting essentially of four elements, whereby an X-ray magnification factor relating to two orthogonal X-ray radiographs, comprising the four elements, taken of bone structure is determined when two of said four elements cover each other in both radiographs, said magnification factor being determined by a distance between two uncovered elements and dependent on movement of said movable arm.

10. An arrangement according to claim 9, wherein said second plate is mounted on a support for attachment to said machine, said support being selectively rotatable about a first axis substantially perpendicular to said second plate and about a second axis substantially perpendicular to the first axis.

11. An arrangement according to claim 10, wherein said support is mountable on a movable frame of said machine, whereby the support is positionable in front of an arrangement for marking of directions and holding of tools for perforation on said machine.

12. An arrangement according to claim 9, wherein said four elements are opaque to X-ray radiation.

13. An arrangement according to claim 12, wherein said four elements are made out of a material opaque to X-ray radiation, said material including at least one of tantalum, lead, and steel alloys thereof.

14. An arrangement according to claim 9, wherein said four elements are placed in a square configuration on said first plate.

15. An arrangement according to claim 9, wherein said four elements are round.

16. A position determining arrangement for bone structure surgery, attachable to a machine with a movable arm, wherein the position determining arrangement is provided with a first plate and a second plate substantially transparent to X-ray radiation in an orthogonal direction and mounted in an orthogonal configuration, said first plate including a plurality of elements provided to determine relative bone structure position, said second plate being mounted on a support for attachment to said machine, said support being selectively rotatable about a first axis substantially perpendicular to said second plate and about a second axis perpendicular to the first axis.

17. An arrangement according to claim 16, wherein an X-ray magnification factor relating to two orthogonal X-ray radiographs, comprising the plurality of elements, taken of bone structure is determined when two of said plurality elements cover each other in both radiographs, said magnification factor being determined by a distance between two uncovered elements and dependent on movement of said movable arm.

18. An arrangement according to claim 16, wherein said support is mountable on a movable frame of said machine, whereby the support is positionable in front of an arrangement for marking of directions and holding of tools for perforation on said machine.

19. An arrangement according to claim 16, wherein said plurality of elements consists essentially of four elements.

20. An arrangement according to claim 19, wherein said four elements are placed in a square configuration on said first plate.

21. An arrangement according to claim 16, wherein said plurality of elements are opaque to X-ray radiation.

22. An arrangement according to claim 16, wherein said plurality of elements are made out of a material opaque to X-ray radiation, said material including at least one of tantalum, lead, and steel alloys thereof.

23. An arrangement according to claim 16, wherein said plurality of elements are round.

* * * * *